United States Patent [19]

Frampton

[11] 4,091,835
[45] May 30, 1978

[54] AUTOKINETIC SAMPLING NOZZLE

[75] Inventor: Charles H. Frampton, Mt. Pleasant, S.C.

[73] Assignee: The United States of America as represented by the Secretary of the Navy, Washington, D.C.

[21] Appl. No.: 759,526

[22] Filed: Jan. 14, 1977

[51] Int. Cl.² ............................................. G05D 7/01
[52] U.S. Cl. ................................. 137/118; 73/422 R; 137/499; 37/517; 137/518
[58] Field of Search ....... 73/421 R, 421.5 R, 421.5 A, 73/422 R; 138/45; 137/517, 518, 521, 499, 118

[56] References Cited

U.S. PATENT DOCUMENTS

| 947,166 | 1/1910 | Smith | 37/521 |
|---|---|---|---|
| 2,303,085 | 11/1942 | Maddox | 73/422 R |
| 2,764,183 | 9/1956 | Gollehon | 137/517 X |
| 3,149,493 | 9/1964 | Mortenson et al. | 73/422 R |
| 3,380,474 | 4/1968 | Mills | 137/521 X |
| 3,684,013 | 8/1972 | Brown | 137/517 X |
| 3,837,363 | 9/1974 | Meronek | 138/45 |
| 3,965,928 | 6/1976 | Siegwart | 137/521 X |

*Primary Examiner*—Robert G. Nilson
*Attorney, Agent, or Firm*—Richard S. Sciascia; Don D. Doty

[57] ABSTRACT

A sampling nozzle is disclosed which includes an inlet valve that automatically adjusts the opening thereof in predetermined inverse porportions to the pressures applied thereto by the fluid and/or other substances being sampled thereby. Whenever a constant pressure suction pump is effectively connected to the outlet thereof, isokinetic sampling is achieved within a system of varying velocities of the aforesaid fluid and/or other substances and, thus, a substantially fixed sampling rate is maintained with respect thereto.

15 Claims, 9 Drawing Figures

AUTOKINETIC SAMPLING NOZZLE

FIELD OF THE INVENTION

The present invention, in general, relates to fluid sampling instruments and, in particular, is an autokinetic fluid sampling device. In even greater particularity, the subject invention consists of a fluid sampling nozzle that automatically adjusts the geometrical configuration of the intake portion thereof in such manner that isokinetic fluid sampling is achieved within a system of varying fluid velocities, while maintaining a substantially fixed fluid sampling rate.

DESCRIPTION OF THE PRIOR ART

Heretofore, in most instances, the sampling of fluids flowing within a pipe, duct, or the like, has been effected by drawing a sample thereof from its stream by means of a conventional isokinetic nozzle located therein which is connected to a suction or vacuum pump. However, in such cases, a most representative sample of the fluid stream can ostensively only be obtained when the velocity of the fluid stream entering said isokinetic nozzle is equal to the velocity thereof at the sampling plane outside said isokinetic nozzle, and this can only be achieved by sizing the sampling entrance area — and, thus, the sampling flow rate — for a given fluid velocity at said sampling plane. Hence, if the velocity of the fluid stream changes, sampling errors occur for those velocities which are different from the nozzle design velocity. And when the fluid being sampled contains particulate matter — even if said particulate matters are sub-micron in size — such errors are usually increased. Therefore, in order to maintain isokinetic conditions at a fixed size sampling nozzle, the sampling flow rate must be varied in proportion to and with the pipe or duct fluid velocity. Of course, varying the sampling flow rate may be accomplished, but it would entail the using of a relatively complex and expensive negative feedback type of control system, including, among other things, a fluid flow sensor, an adjustable fluid flow regulator valve, and a controller for governing the suction pump flow rate, all of which are expensive to purchase, use, and maintain, and all of which are subject to faulty operation. Hence, it may readily be seen that there is a need for an improved method and means for sampling fluids containing or not containing solid particles, regardless of their size.

SUMMARY OF THE INVENTION

The instant invention overcomes many of the disadvantages of the aforementioned prior art, in that instead of being an isokinetic nozzle, it is an autokinetic nozzle which when subjected to the forces of fluid flowing within a closed system — that is, in a pipe, duct, chamber, or the like — is automatically movably responsive thereto in such manner that the fluid dynamic forces occurring therein vary the entrance area thereof, so as to obtain a desired constant fluid sampling rate, or in the alternative, if so desired, to develop a predetermined rate of change of fluid sampling rate for a variable rate of flow of said fluid.

Therefore, an object of this invention is to provide an improved method and means for sampling fluid flowing within a field.

Another object of this invention is to provide an autokinetic fluid nozzle.

Another object of this invention is to provide a simple and accurate method and means for sampling at a constant fluid sampling rate a fluid, containing or not containing particulate matter, within a system that is subject to fluid velocity changes.

Still another object of this invention is to provide a nozzle that automatically adjusts the area and geometrical configuration of the inlet thereof in such manner as to facilitate obtaining isokinetic fluid sampling within a dynamic fluid environment.

Another object of this invention is to provide a relatively simple and accurate method and means for sampling at a substantially constant sampling rate a gas or other fluid, whether or not containing liquids and/or particulate matters, that is located within a predetermined ambient environmental system or container that is subject to velocity changes therein with respect thereto.

A further object of this invention is to provide an autokinetic nozzle which self-adjusts its inlet area to yield isokinetic conditions in a variable velocity flow field, so as to function at a substantially constant volumetric sample flow rate.

Another object of this invention is to provide an autokinetic nozzle that is easily and economically constructed, operated, and maintained.

Another object of this invention is to provide a simple autokinetic nozzle which may be used with a fixed volumetric sampling pump.

Other objects and many of the attendant advantages of this invention will be readily appreciated as the same becomes better understood by reference to the following detailed description when considered in connection with the accompanying drawings wherein:

DESCRIPTION OF THE PREFERRED EMBODIMENTS

Figure 1:
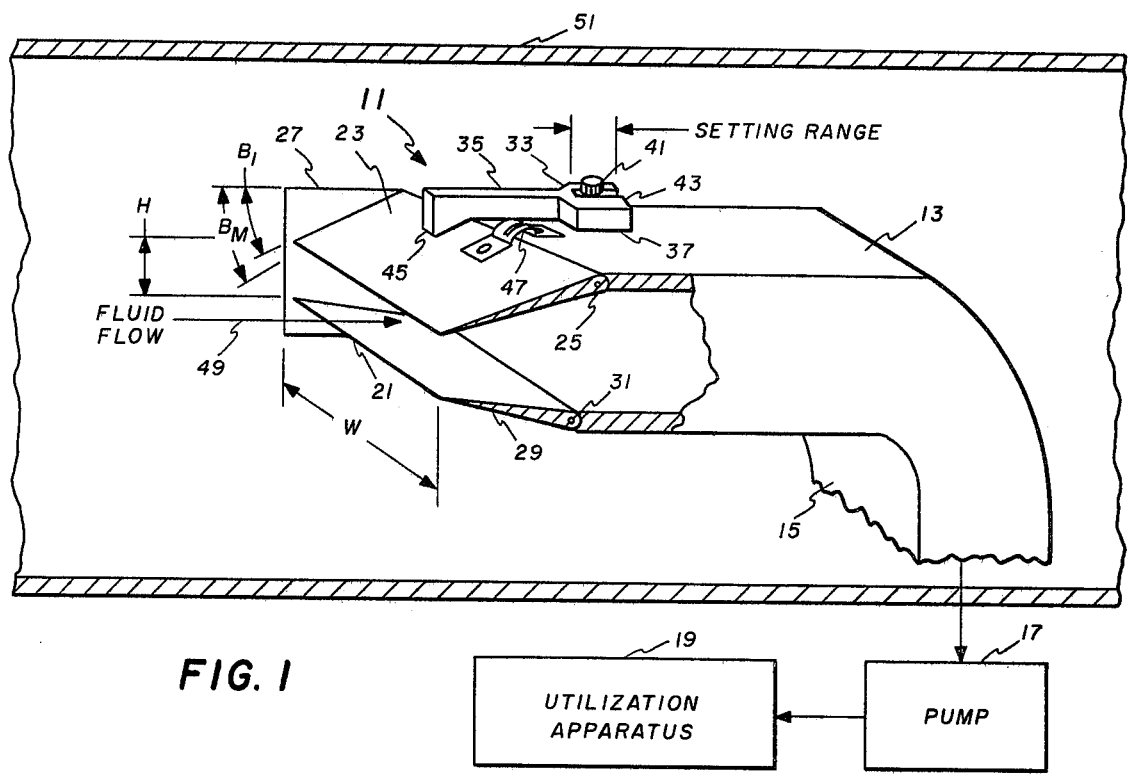
FIG. 1 is a perspective view, with parts broken away, of the isokinetic nozzle constituting the subject invention.

At the outset, because some of the elements and components discussed herein and depicted in most of the figures of the drawing are the same or similar, they have been identified by like reference numerals, in order to facilitate the understanding of the various respective relationships thereof with their associated parts.

Referring now to FIG. 1, there is shown one species of autokinetic nozzle 11 as having a support or duct portion 13, the lower effluent extremity 15 of which is adapted to be effectively connected to a fixed volumetric vacuum, suction, or other type pump 17, and/or any other device (not shown) intended to directly receive the fluid sample obtained by said autokinetic nozzle 11. Of course, as is conventional in the art, the output of pump 17 may be connected to any suitable apparatus 19 adapted to make some use of the aforesaid obtained fluid sample.

At the inlet end 21 of autokinetic nozzle 11 is a movable nozzle flapper valve or upper lip 23 that is movably connected to duct 13 by means of any suitable hinge 25 or other flexible member, and preferably integrally connected to the inlet portion duct 13 are a pair of nozzle side lips 27, only one of which can be seen in FIG. 1 because the other has been broken away for disclosure purposes.

Also located at the inlet end of nozzle 11 is a flapper valve or lower lip 29 which may either be movably connected thereto like upper lip 23, or may be integrally or otherwise connected thereto in a fixed arrangement therewith. If movable, lip 29 would use another hinge 31 as a connection means to duct 13, as well as have other elements associated therewith but not shown in FIG. 1 because they would be hidden on the underside of nozzle 11. Obviously, it would be well within the purview of the artisan having the benefit of the teachings presented herewith to make lip 29 either movable or fixed, as desired, with respect to duct 13.

A motion limiter 33 having an elongated arm 35 at the front end thereof and a bifurcated or slotted extremity 37 at the rear end thereof is adjustably connected for forward and rearward movement as a result of a threaded set screw 41 extending through a slot 43 and into a threaded hole (not shown) in duct 13. In order to maintain movable lip 23 in a partially closed position, the forward end of arm 35 has a lower lip or extension 45 intended to abut against the upper surface of said lip 23 and, hence, limit its rotational movement in such manner that the area (W × H) of inlet 21 thereof is held to a predetermined maximum, depending on the position of set screw 41 within slot 43. This function may also be produced by any other axially or rotationally moving and locking member.

A spring 47 — or other resilient moment producing device — resiliently holds upper lip 23 against extension 45 of motion limiter 37 in accordance with a predetermined spring rate designed therein for such purpose, as will be discussed again more fully subsequently.

Nozzle 11 may be used, of course, to sample any fluid or other appropriate substance or material 49 or combination thereof flowing within a pipe 51 or other container within which it is deployed. Obviously, the means for installing and mounting a fluid sampling nozzle like the subject nozzle 11 within pipe 51 at any given location and attitude is conventional and, thus, already well known to the artisan. Hence, no further disclosure thereof is deemed necessary at this time.

Figure 2:
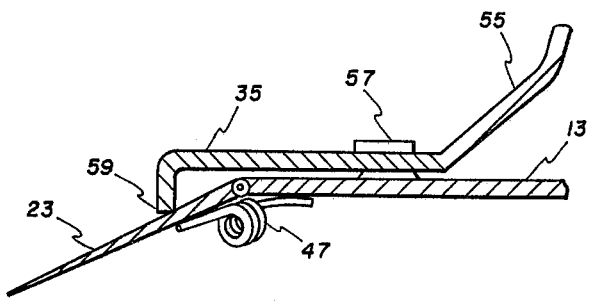
FIG. 2 is a cross-sectional view of a moment amplifying motion limiter that may or may not be substituted for the motion limiter of FIG. 1.

As depicted in FIG. 2, the aforementioned motion limiter 35 of FIG. 1 may be constructed in such manner as to have a rearwardly and upwardly extending plate or vane 55 attached thereto or provided separately, if so desired. Said vane 55, of course, effectively increases the equivalent flat plate area presented to the ambient fluid flowing by and against it, the forward extremity of duct 13, and upper valve flapper 23 in combination, thereby amplifying the fluid dynamic moment loading on said valve flapper 23 at location 59. A linear bearing, bushing, sleeve or other device 57 facilitates movement of the moment amplifying device.

Figure 3:
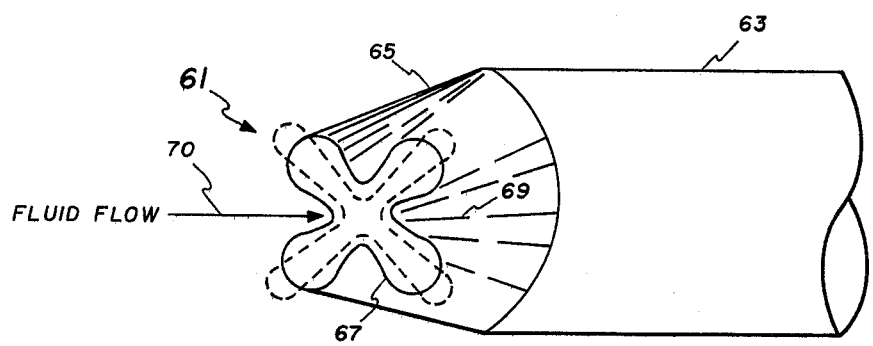
FIG. 3 is a perspective view of another species of the instant invention.

FIG. 3 illustrates another species of the subject invention 61. Very simply, it contains a duct 63 with a flexible, resilient boot 65 attached to the forward end thereof. Boot 65 has an inlet or mouth 67 contoured in such manner as to cause boot 65 to be forwardly pointed or tapered, as a result of one or more predetermined folds 69. As the fluid 70 to be sampled flows against the forward tapered surface of boot 65, the inlet or mouth configuration thereof is made smaller and perhaps takes a shape similar to that shown (by way of example) by dashed line 71. Of course, the material type, thickness, and resiliency selected for tapered boot 65 may be such as will enable it to be compressed in proportion to fluid flow, thereby making the area of inlet 67 to be inversely proportional to said fluid flow as it changes in velocity, thus making nozzle 61 be an autokinetic nozzle instead of an isokinetic nozzle.

As previously indicated, in order to make autokinetic nozzle 11 a nozzle which self-adjusts upper lip 23 — and/or lower lip 21, if movable about hinge 31 — so as to sample a substantially constant volume of fluid having varying velocities, spring 37 — and any spring associated with lower lip 21, if movable — would have to be designed to vary the entrance or affluent inlet area (H × W) to nozzle 11 in inverse proportion therewith. For purposes of keeping this disclosure as simple as possible, it will be considered that only lip 23 is movable, and, thus, only spring 47 need be designed accordingly. Nevertheless, it should be understood that two (or more) springs (or other resilient means) and two or more lips if the opening were of an iris type, would have to be properly designed to meet operational requirements in the event nozzle 11 were designed to be symmetrical and, therefore, to have both lips 21 and 23 move automatically to properly vary entrance area H × W for a given constant sampling flow rate of suction pump 17, so as to effectively maintain an isokinetic condition thereat.

Figure 4:
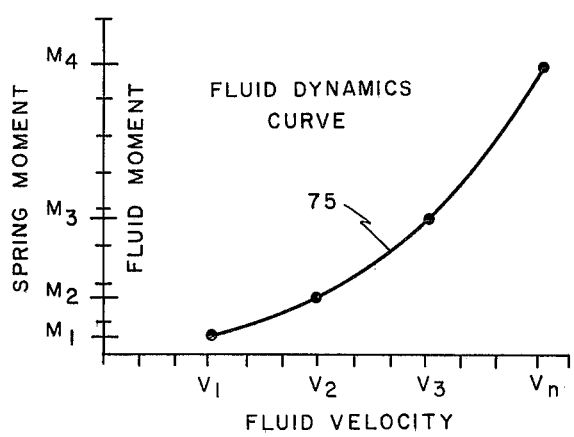
FIG. 4 is a graphical illustration of a fluid dynamics curve which may be used to acquire spring moments from various fluid velocities.
Figure 5:
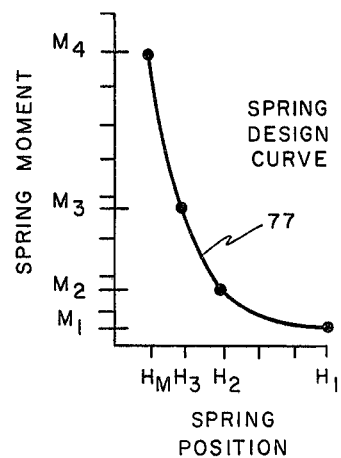
FIG. 5 is a graphical illustration of a spring design curve plotted in terms of spring moments vs. spring positions.

As best seen from the fluid dynamic characteristics of FIG. 4, for any given size nozzle, the dynamic fluid loading on lip 23 produces moments (M) about hinge 25 at various fluid velocities (V), and said fluid moments (M) may be obtained empirically or analytically. And, because said moments are equal to the moments of spring 47, they may be used to plot a required spring moment vs. a fluid velocity curve 75 and, thus, design spring 47 for various areas (H × W) of the inlet to nozzle 11. Since, in this case, only angle $\beta$ may be changed — say, from $\beta_1$ to $\beta_n$ — to change the inlet area, and since width W remains the same, for any given size autokinetic nozzle, a spring design curve 77 of FIG. 5 is plotted with moment M as the ordinate and height H as the abscissa. Hence, from both FIGS. 4 and 5, the various fluid and spring moments M and nozzle heights H correspond to various fluid velocities (V). And, consequently, if spring 47 is designed to have the characteristics of the spring design curve of FIG. 5, an isokinetic condition will be maintained at the entrance of nozzle 11 for a constant suction at pump 17.

Theory of Operation

Figure 6:
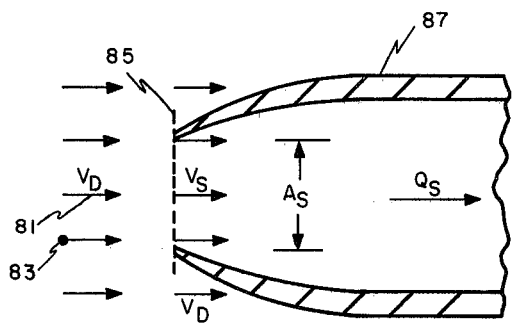
FIGS. 6, 7, and 8 respectively depict various theoretical fluid flow conditions which may exist with respect to isokinetic sampling nozzles.

A most representative sample of a fluid stream, and especially one containing particles uniformly distributed therein, must be taken under a condition which prevails where the velocity of the stream entering the sampling nozzle is equal to the velocity at the fluid stream sampling plane outside the nozzle. This is achieved by sizing the sampling nozzle affluent area and the sampling flow rate of a fluid 81, with or without particles 83, as a function of the fluid velocity at the sampling plane 85 and outside the nozzle 87, as is depicted in FIG. 6. Then:

$$Q_s = A_s V_d, \quad (1)$$

where under isokinetic conditions
$V_d = V_s$, and
$V_d$ = fluid velocity in the pipe from which the fluid is being sampled,
$V_s$ = fluid velocity in the sampling nozzle,
$Q_s$ = volumetric flow rate to the suction pump,
$A_s$ = area of the sampling nozzle.

Such condition, as previously suggested, is achieved by sizing the sampling nozzle area — and, thus, the sampling flow rate — as a function of the fluid velocity at the aforesaid sampling plane 85 and outside sampling nozzle 87.

Figure 7:
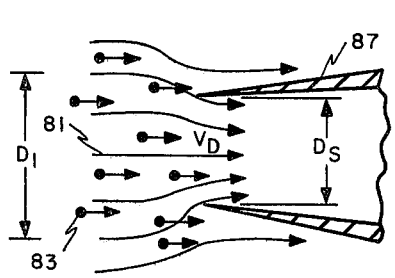
Figure 8:
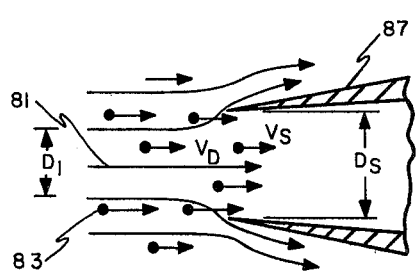

The effects of erroneously sizing sampling nozzle 87 as applied to sampling fluid stream 81 — say, containing particulate matter 83 — are shown in FIGS. 7 and 8.

Figure 9:
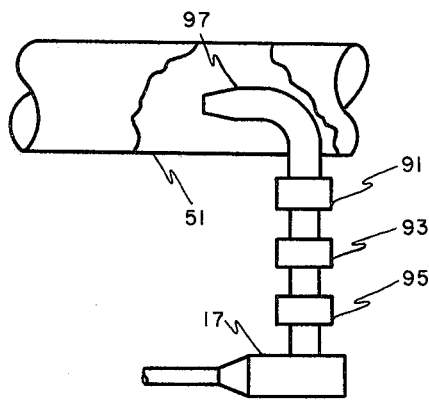
FIG. 9 illustrates a typical fluid sampling system which may or may not include the nozzle constituting the instant invention.

In FIG. 7, the situation is shown where the fluid velocity in the sampling nozzle, $V_s$, is greater than the fluid velocity, $V_d$, in the pipe from which the fluid is being sampled; and in FIG. 8, the situation is shown where the fluid velocity in the sampling nozzle, $V_s$, is less than the fluid velocity, $V_d$, in the pipe from which the fluid is being sampled. In this particular instance, for the purpose of illustrating a typical situation, the fluid stream 81 is considered to be air 81 in a conventional ventilation duct with relatively low velocities, such that the flowing air behaves as an incompressible gas, and the particles 83 are assumed to be sub-micron solids 83. Such heavier solid particles 83 possess inertia forces that are higher than the viscous forces of the fluid 81, which, of course, in the situations being described, are trying to abruptly redirect them immediately upstream of the nozzle entrance. The fluid being sampled in both cases is that occurring within the boundary dimension defined as $D_1$; thus, the particles being sampled in both cases are those occurring within the boundary dimension defined as $D_1$. This, then, results in an erroneously low particle density count in the sampled fluid in FIG. 7, where $V_s > V_d$, and an erroneously high particle density count in the sampled fluid in FIG. 8, where $V_s < V_d$. Therefore, it may readily be seen that errors in measurement would occur, in the event the entrance area of any isokinetic nozzle was not correct for the particular velocity of the fluid being sampled at any given instant; moreover, if the velocity thereof varied, then such measurement would be in error at all times other than the one particular velocity for which its entrance area are designed. Thus, it may generally be said that using isokinetic nozzles has considerable limitations, in that — as shown in FIGS. 7 and 8 — fluid velocity changes in a pipe or ventilation duct yield non-isokinetic conditions at the sampling entrance thereof. And, furthermore, to maintain isokinetic conditions at the entrance or inlet of fixed size sampling nozzles, the sampled fluid flow rate would have to be varied proportionally to the duct fluid velocity. That could be done, but considerable additional apparatus — such as, for example, a filter or sampling chamber 91, a fluid flow control valve 93, a flowmeter 95, and perhaps other elements as well — would be required, as depicted in FIG. 9, if nozzle 97 shown therein were an isokinetic nozzle located in a pipe or duct 51. On the other hand, if nozzle 97 were similar to properly designed autokinetic nozzles 11 and 61 of FIGS. 1 and 3, respectively, two preferred embodiments of the autokinetic nozzle constituting this invention, no such problems or errors would occur, and chamber 91, valve 93, and controller or flowmeter 95 would not be necessary, thereby simplifying the sampling system thereof considerably over that which would be required if isokinetic prior art nozzles were so employed.

Mode of Operation

The operation of the present invention will now be discussed briefly in conjunction with FIGS. 1 through 3 of the drawing.

When nozzle 11 is installed in duct 51 as shown in FIG. 1, and suction pump 17 draws a fluid sample at constant rate, very simply, whenever the flow of fluid 49 varies, the dynamic forces thereof against the upper surface of lip 23 causes it to move against or with the urging of spring 47 to close or open the entrance nozzle 11 in such manner that the flow rate therethrough remains substantially constant. Hence, the sample rate thereof remains constant, too. Of course, if vane 55 is integrally or otherwise suitably attached to motion limiter 35 — as illustrated in FIG. 2 — the dynamic influence of the flowing fluid 49 against the upper surface of lip 23 is enhanced. Thus, spring 47 (or other appropriate resilient means) may be made to be more compatible with certain types of fluid flow sampling, if desired.

Likewise, fluid 70 flowing against the resilient conical frontal surfaces of autokinetic nozzle 61 of FIG. 3 will cause them to collectively acquire a new integrated geometrical configuration and effectively pinch inlet 67 thereof, so that it will become smaller by taking a form somewhat similar to inlet form 71 shown by the dashed lines. Of course, decreasing the area of inlet 67 increases the fluid velocity proportionally therethrough and, hence, accurate sampling is effected, provided the resiliency of the material forming said conical frontal surfaces is properly selected and designed. In view of the foregoing, however, it would be obvious for the artisan so to do if he had the benefit thereof.

From the above, it may readily be seen that the subject nozzle automatically restricts the fluid flowing therethrough in some predetermined inverse proportion with the flow thereof in the duct ambient thereto and, therefore, a constant fluid sampling rate is effected thereby whenever suction pump 17 (FIG. 1) is used in conjunction therewith.

Obviously, many modifications and variations of the present invention are possible in the light of the above teachings; for instance, one variation being that the sampling velocity may be a predetermined factor above the duct velocity (super-kinetic) for some desired reason, or effect or the sampling velocity may be a predetermined factor below the duct velocity (sub-kinetic) for some desired reason or effect. A purpose of super or sub-kinetic sampling could be to desirably decrease or amplify particle count per sample. It is, therefore, to be understood that within the scope of the appended claims the invention may be practiced otherwise than as specifically described.

What is claimed is:

1. An autokinetic fluid sampling device, comprising in combination:

duct means having an open fluid inlet at one end thereof and an open fluid outlet at the other end thereof;

means connected to said duct means for effectively varying the area of the open fluid inlet thereof in predetermined inverse proportion to the velocity of the flowing fluid being sampled in automatic response to the impact of said flowing fluid thereon; and adjustable means effectively connected to said duct means adapted for timely engagement with said fluid inlet varying means in such manner as to limit the maximum area of the aforesaid open fluid inlet, said adjustable means including an elongated arm having a lower extending lip connected to the extremity thereof that is adjacent to said fluid inlet varying means, and a slotted extension connected to the extremity thereof that is opposite the one to which said lower extending lip is connected; a threaded hole located in the aforesaid duct means; and a threaded set screw extending through the slot of the slotted extension of said elongated arm and screwed to the aforesaid threaded hole, so as to firmly hold said elongated arm in a predetermined disposition with respect to said duct means and the aforesaid fluid inlet varying means.

2. The device of claim 1, wherein said means connected to said duct means for effectively varying the area of the open fluid inlet thereof in predetermined inverse proportion to the velocity of the flowing fluid being sampled in automatic response to the impact of said flowing fluid thereon comprises a resilient boot having a forward taper and a flexible open mouth at the apex thereof, the opening of which is predeterminedly inversely variable with the impact of the fluid being sampled against the outside surface of the aforesaid resilient boot.

3. The device of claim 1, wherein said means connected to said duct means for effectively varying the area of the open fluid inlet thereof in predetermined inverse proportion of the velocity of the flowing fluid being sampled in automatic response to the impact of said flowing fluid thereon comprises:

a flapper valve of predetermined geometrical configuration rotatably connected to said duct means in such manner that it will be moved toward the position of effectively closing the open fluid inlet of said duct means as a consequence of the flowing fluid being sampled impacting thereon; and resilient means connected between said duct means and said flapper valve for the continuous predetermined urging thereof toward the position of effectively further opening the open fluid inlet of said duct means in opposition to the impact of the flowing fluid being sampled on said flapper valve.

4. The device of claim 3, wherein said resilient means connected between said duct means and said flapper valve for the continuous predetermined urging thereof toward the position of effectively further opening the open fluid inlet of said duct means in opposition to the impact of the flowing fluid being sampled on said flapper valve comprises a spring having a predetermined spring rate.

5. The device of claim 1, wherein said means connected to said duct means for effectively varying the area of the open fluid inlet thereof in predetermined inverse proportion of the velocity of the flowing fluid being sampled in automatic response to the impact of said flowing fluid thereon comprises:

a plurality of flapper valves of predetermined geometrical configurations connected to said duct means in such manners, respectively, that they will be moved toward positions of effectively closing the open fluid inlet of said duct means as a consequence of the flowing fluid being sampled impacting thereon; and resilient means respectively connected between said duct means and said plurality of flapper valves for the continuous predetermined urging thereof toward the positions of effectively further opening the open fluid inlet of said duct means in opposition to the impact of the flowing fluid being sampled on said plurality of flapper means.

6. The device of claim 5, wherein said resilient means respectively connected between said duct means and said plurality of flapper valves for the continuous predetermined urging thereof toward the positions of effectively further opening the open fluid inlet of said duct means in opposition to the impact of the flowing fluid being sampled on said plurality of flapper valves comprises a like plurality of springs, each of which has a predetermined spring rate.

7. The invention of claim 1, further characterized by suction pump means connected to the open fluid outlet of said duct means.

8. The invention of claim 7, further characterized by a utilization apparatus connected to the output of said suction pump means.

9. The invention of claim 1, further characterized by a rearwardly and upwardly extending vane contiguously disposed with respect to said fluid inlet area limiting means for amplifying the fluid dynamic loading of the aforesaid fluid inlet varying means.

10. An autokinetic nozzle adapted for sampling at a constant rate from within a pipe a flowing fluid containing solid particulate matter, the velocities of which vary from time to time, comprising in combination:

duct means having an open fluid inlet at one end thereof and an open fluid outlet at the other end thereof;

suction pump means connected to the open fluid outlet of said duct means for effecting a substantially constant fluid pressure thereat which is less than the fluid pressure within said duct means;

valve means effectively connected to the open inlet end of said duct means for effectively varying the size of said open fluid inlet in such manner automatically in response to the composite of the forces applied thereto by the fluid flowing within the aforesaid pipe as to close said autokinetic nozzle to sample said flowing fluid at a substantially constant rate that is equal to the suction rate of the aforesaid suction pump means, regardless of the fluctuations of the velocities of the fluid flowing within said pipe.

11. The invention of claim 10, further characterized by a utilization apparatus connected to the output of said suction pump.

12. The invention of claim 10, further characterized by means effectively connected to said duct means for amplifying the response of the aforesaid valve means to the composite fluid forces applied thereto.

13. The autokinetic system for sampling flowing substances from within a container, wherein the velocities thereof fluctuate from time to time, comprising in combination:

a container within which substances flow;

an open-ended duct having an affluent end into which a sample of the aforesaid substances flow and an effluent end out of which said sample of substances flow, said open-ended duct being mounted within said container in such manner as to partially extend through the wall thereof;

first valve means effectively connected to the affluent end of said open-ended duct means for effectively varying the area of the open affluent end thereof in a predetermined manner and in predetermined response to forces applied thereto by the aforesaid flowing substances;

second valve means effectively connected to the affluent end of said open-ended duct means for effectively varying the area of the open affluent end thereof not varied by said first valve means in a predetermined manner and in predetermined response to forces applied thereto by the aforesaid flowing substances;

first resilient means interconnecting said duct and said first valve means for the urging of said first valve means toward an open position in accordance with a first predetermined resiliency rate;

second resilient means interconnecting said duct and said second valve means for the urging of said second valve means toward an open position in accordance with a second predetermined resiliency rate;

first stop means adjustably connected to said duct and adapted to timely contact said first valve means in such manner as to limit the maximum open position thereof;

second stop means adjustably connected to said duct and adapted to timely contact said second valve means in such manner as to limit the maximum open position thereof; and means effectively connected to the effluent end of the aforesaid open-ended duct for creating a pressure thereat which is less than the pressure within the aforesaid container.

14. The invention of claim 13, further characterized by first and second means respectively connected to said first and second stop means for effectively magnifying the forces applied to said first and second valve means by the aforesaid flowing substances.

15. The device of claim 14, wherein each of said first and second means respectively connected to said first and second stop means for effectively magnifying the forces applied to said first and second valve means by the aforesaid flowing substances comprises a vane extending outwardly from said duct at a predetermined angle.

* * * * *